United States Patent [19]

Manabe et al.

[11] Patent Number: 4,946,867
[45] Date of Patent: Aug. 7, 1990

[54] CYANOACETAMIDE DERIVATIVE, AND PLANT DISEASE PROTECTANT COMPRISING THE SAME AS AN ACTIVE INGREDIENT

[75] Inventors: Akio Manabe; Masato Mizutani, both of Toyonaka; Kiyoto Maeda, Nishinomiya; Tadashi Ooishi, Urawa; Hirotaka Takano, Sanda, Osamu Kirino deceased, late of Toyonaka, by Takako Kirino, Toyonaka, legal representative, all of Japan

[73] Assignee: Sumitomo Chemical Company, Limited, Osaka, Japan

[21] Appl. No.: 234,598

[22] Filed: Aug. 22, 1988

[30] Foreign Application Priority Data

| Sep. 7, 1987 | [JP] | Japan | 62-224430 |
| Nov. 5, 1987 | [JP] | Japan | 62-280549 |
| Apr. 12, 1988 | [JP] | Japan | 63-89564 |
| May 27, 1988 | [JP] | Japan | 63-130796 |
| Jun. 7, 1988 | [JP] | Japan | 63-141171 |

[51] Int. Cl.$^5$ .................. A61K 31/165; C07C 103/00
[52] U.S. Cl. ..................................... 514/521; 558/392
[58] Field of Search .......................... 558/392; 514/521

[56] References Cited

FOREIGN PATENT DOCUMENTS 63-72661  4/1988  Japan ..................... 558/392
0072663  4/1988  Japan ..................... 558/392

OTHER PUBLICATIONS

J. Pesticide Sci., 12, 79–84 (1987).

*Primary Examiner*—Mary C. Lee
*Assistant Examiner*—J. Richter
*Attorney, Agent, or Firm*—Stevens, Davis, Miller & Mosher

[57] ABSTRACT

A cyanoacetamide derivative of the formula,

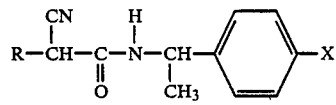

wherein R represents a $C_2$–$C_6$ alkyl, $C_2$–$C_6$ alkenyl, $C_2$–$C_6$ alkynyl or $C_3$–$C_6$ cycloalky group, and X represents a chlorine or bromide atom or a trifluoromethyl or lower fluoroalkoxy group and a plant disease protectant comprising the same are disclosed. The cyanoacetamide derivative provided according to the present invention has an extremely high controlling activity against various plant diseases, particularly against rice blast (*Pyricularia oryzae*).

20 Claims, No Drawings

CYANOACETAMIDE DERIVATIVE, AND PLANT DISEASE PROTECTANT COMPRISING THE SAME AS AN ACTIVE INGREDIENT

The present invention relates to a novel cyanoacetamide derivative, a method for producing the same and a plant disease protectant comprising the same as an active ingredient.

Various plant disease protectants have been developed till now, but they are not always said to be satisfactory in terms of efficacy, etc.

The present inventors have extensively studied to develop a compound having a high controlling activity against plant diseases, and as a result, have found that a cyanoacetamide derivative represented by the formula (I) (hereinafter referred to as the present compound),

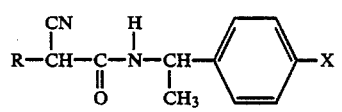

wherein R represents a $C_2$–$C_6$ alkyl, $C_2$–$C_6$ alkenyl or $C_2$–$C_6$ alkynyl group or a $C_3$–$C_6$ cycloalkyl group, and X represents a chlorine or bromine atom or a trifluoromethyl or lower fluoroalkoxy group.

The cyanoacetamide derivative of the claimed invention has high foliage protecting and disease controlling activities and systemic disease controlling activity particularly against rice blast (*Pyricularia oryzae*). The present inventors thus attained to the present invention.

Among the present compounds, those which are more preferred in terms of the controlling activity are compounds in which R in the formula (I) is a $C_3$–$C_5$ secondary or tertiary alkyl group or a $C_3$–$C_5$ secondary or tertiary alkenyl group, or a $C_3$–$C_5$ secondary or tertiary alkynyl group, and those which are particularly preferred are compounds represented by the following formulae:

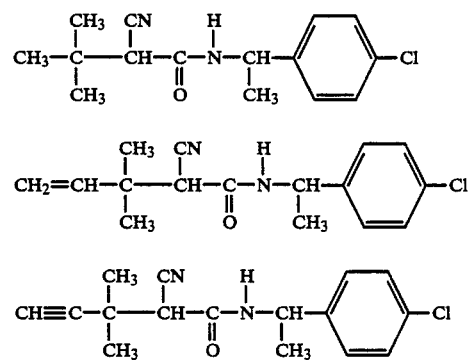

The present compounds have an extremely high controlling activity particularly against rice blast (*Pyricularia oryzae*). Other plant diseases which can be controlled by the present compounds include helminthosporium leaf spot of rice (*Cochliobolus miyabeanus*), scab of apple (*Venturia inaequalis*), scab of pear (*Venturia nashicola*), anthracnose of Japanese persimmon (*Gloeosporium kaki*), anthracnose of melons (*Colletotrichum lagenarium*), anthracnose of kidney bean (*Collectotrichum lindemuthianum*), leaf spot of peanut (*Mycosphaerella personatum*), brown leaf spot of peanut (*Cercospora arachidicola*), anthracnose of tobacco (*Colletotrichum tabacum*), cercospora leaf spot of beet (*Cercospora beticola*), etc.

A method for producing the present compounds is explained in detail below.

The present compounds can be obtained by reacting an α-methylbenzylamine derivative represented by the formula (II),

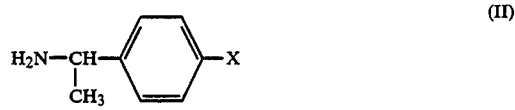

wherein X represents the same meaning as described above, with an α-substituted cyanoacetic acid represented by the formula (III),

wherein R represents the same meaning as described above,
or its reactive derivative in the presence of one or more reaction assistants if necessary.

In the above reaction, the α-substituted cyanoacetic acid represented by the formula (III) or its reactive derivative includes the corresponding carboxylic acid, acid anhydride, acid chloride, acid bromide and carboxylic acid esters (e.g. methyl ester, ethyl ester), etc. As examples of the reaction assistant, there are mentioned the following compounds depending on the type of the α-substituted cyanoacetic acid represented by the formula (III) or its reactive derivative: Dicyclohexylcarbodiimide, 1-ethyl-3-(3-dimethylaminopropyl)-carbodiimide hydrochloride, 1,1'-carbonyldiimidazole, phosphorus pentachloride, phosphorus trichloride, phosphorus oxychloride, thionyl chloride, phosgene, sodium hydroxide, potassium hydroxide, sodium methylate, sodium ethylate, triethylamine, pyridine, quinoline, N,N-dimethylaniline, N,N-diethylaniline, N-methylmorpholine, etc.

In the above reaction, normally, the reaction temperature is from 0° to 200° C.; the reaction time is from 0.1 to 24 hours. As to the amount of the reagents used for the reaction, the amount of the α-methylbenzylamine derivative represented by the formula (II) is from 1 to 1.2 moles based on 1 mole of the α-substituted cyanoacetic acid represented by the formula (III) or its reactive derivative, and that of the reaction assistant is from 1 mmole to 5 moles based on the same.

In the above reaction, a reaction solvent is not always necessary, but generally, the reaction is carried out in the presence of a solvent.

Examples of the usable solvent include solvents such as aliphatic hydrocarbons (e.g. hexane, heptane, ligroin), aromatic hydrocarbons (e.g. benzene, toluene, xylene), ethers (e.g. diethyl ether, diisopropyl ether, tetrahydrofuran, dioxane, diethylene glycol dimethyl ether), halogen-containing solvents (e.g. dichloromethane, chloroform, carbon tetrachloride, 1,2-dichloroethane, chlorobenzene), N,N-dimethylformamide, dimethyl sulfoxide, acetonitrile, water, etc. and mixtures thereof.

After the completion of the reaction, the desired present compounds can be obtained by carrying out the usual workup such as extraction, concentration, filtration, etc. and additionally, if necessary, column chromatography, recrystallization, etc.

Method B

Among the present compounds, those which are represented by the formula (I'),

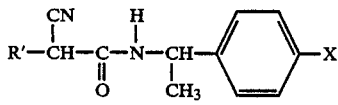

wherein R' represents a $C_2$–$C_6$ primary or secondary alkyl, a $C_2$–$C_6$ primary or secondary alkenyl or a $C_2$–$C_6$ primary or secondary alkynyl group or a $C_3$–$C_6$ cycloalkyl group, and X represents the same meaning as described above, can also be obtained by reacting a cyanoacetamide derivative represented by the formula (IV),

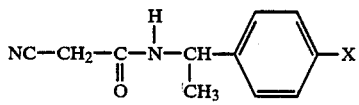

wherein X represents the same meaning as described above, with an alkylating agent represented by the formula (V), $$R'-L \quad (V)$$

wherein R' represents the same meaning as described above, and L represents an eliminating group such as a chlorine, bromine or iodine atom or methanesulfonyloxy or p-toluenesulfonyloxy group, in the presence of base.

The base used in the above reaction includes, for example, alkali metal hydrides (e.g. sodium hydride), etc.

In the above reaction, normally, the reaction temperature is from $-10°$ to $100°$ C.; the reaction time is from 0.1 to 24 hours. As to the amount of the reagents used for the reaction, the amount of the alkylating agent represented by the formula (V) is from 1 to 1.5 moles based on 1 mole of the cyanoacetamide derivative represented by the formula (IV), and that of the base is from 1 to 1.2 moles based on the same.

Examples of the usable solvent in the above reaction include aliphatic hydrocarbons (e.g. hexane), aromatic hydrocarbons (e.g. benzene, toluene, xylene), ethers (e.g. tetrahydrofuran, dioxane, 1,2-dimethoxyethane), aprotic polar solvents (e.g. N,N-dimethylformamide), etc.

After the completion of the reaction, the desired present compounds can be obtained by carrying out the usual workup such as extraction, concentration, filtration, etc. and additionally, if necessary, column chromatography, recrystallization, etc.

Some of the present compounds are shown below.

PRODUCTION EXAMPLE 1

(Compound No. 2)

0.80 Gram (4 mmoles) of 1-(4-bromophenyl)-ethylamine and 0.48 g (4.8 mmoles) of triethylamine were dissolved in 10 ml of ether and cooled with ice. To this solution was added dropwise 0.64 g (4 mmoles) of α-cyano-tert-butylacetyl chloride, followed by stirring at room temperature for 2 hours. After the reaction had been completed, addition of ether, washing with water, drying over anhydrous magnesium sulfate and removal of the solvent were carried out in this order to obtain 1.25 g of a viscous oil. Purifying this oil by column chromatography on silica gel (eluent, hexane:ethyl acetate=5:1) gave 0.94 g of N-[1-(4-bromophenyl)ethyl]-2-cyano-3,3-dimethylbutanamide (yield, 73%).

m.p. 102°–104° C.

$^1$H-NMR (CDCl$_3$/TMS): δ(ppm) 1.11 (s, 9H), 1.45 (d, J=7 Hz, 3H), 3.17 (s, 1H), 4.7–5.25 (m, 1H), 6.67 (br d, 1H), 7.0–7.6 (m, 4H).

Mass spectrum (m/e, 70 eV): 322(M$^+$), 265, 198, 183, 104.

PRODUCTION EXAMPLE 2

(Compound No. 13)

0.60 Gram (3 mmoles) of 1-(4-bromophenyl)ethylamine and 0.34 g (3.3 mmoles) of triethylamine were dissolved in 10 ml of acetonitrile and cooled with ice. To this solution was added dropwise 0.48 g (3 mmoles) of α-cyano-sec-butylacetyl chloride, followed by stirring at room temperature for 2 hours. After the reaction had been completed, addition of ethyl acetate, washing with water, drying over anhydrous magnesium sulfate and removal of the solvent were carried out in this order to obtain 1.07 g of a viscous oil. Purifying this oil by column chromatography on silica gel (eluent, hexane:acetone=5:1) gave 0.90 g of N-[1-(4-bromophenyl)ethyl]-2-cyano-3-methylpentanamide.

$^1$H-NMR (CDCl$_3$/TMS): δ(ppm) 0.65–1.8 (m, 11H), 1.8–2.4 (m, 1H), 3–3.5 (m, 1H), 4.7–5.3 (m, 1H), 6.2–6.7 (m, 1H), 6.9–7.6 (m, 4H)

Mass spectrum (m/e, 70 eV): 322(M$^+$), 307, 265, 198, 183, 104.

PRODUCTION EXAMPLE 3

(Compound No. 9)

0.89 Gram (4 mmoles) of N-[1-(4-chlorophenyl)-ethyl]-2-cyanoacetamide was dissolved in 5 ml of N,N-dimethylformamide (DMF) and cooled with ice. Under a nitrogen atmosphere, 0.17 g (4.2 mmoles) of sodium hydride (60% in oil) was added thereto, followed by stirring for 30 minutes with ice-cooling. Subsequently, 0.73 g (4.8 mmoles) of cyclopentyl bromide was added thereto and the mixture was stirred for 30 minutes with ice-cooling. Thereafter the ice bath was removed and stirring was continued for further 4 hours. After the reaction had been completed, water was added to the reaction mixture, which was then extracted with ethyl acetate. Then the extract was washed twice with brine. The organic layer was dried and concentrated, and to the residue was added a hexane-acetonitrile solution, followed by stirring and liquid-liquid separation. Concentrating the acetonitrile layer gave 1.08 g of a crystalline material. Purifying this material by column chromatography on silica gel (eluent, hexane:ethyl acetate=5:1) gave 0.58 g of N-[1-(4-chlorophenyl)ethyl]-2-cyano-2-cyclopentylethanamide.

m.p. 106°–108° C.

$^1$H-NMR (DMSO-d$_6$/TMS): δ(ppm) 0.8–2.0 (m, 11H), 2.1–2.6 (m, 1H), 3.60 (d, J=9 Hz, 1H), 4.6–5.2 (m, 1H), 7.33 (br s, 4H), 8.7 (br d, 1H).

PRODUCTION EXAMPLE 4

(Compound No. 22)

0.97 Gram (6 mmoles) of 1,1'-carbonyldiimidazole was added in small portions to a solution of 0.76 g (5 mmoles) of 2-cyano-3,3-dimethyl-4-pentenoic acid in 5 ml of dry tetrahydrofuran. The mixture was stirred at room temperature for 1 hour. To this solution was added dropwise 0.78 g (5 mmoles) of 1-(4-chlorophenyl)ethylamine, followed by stirring at room temperature for 2 hours. After the reaction had been completed, ether was added to the reaction solution, which was then successively washed with a 5% aqueous hydrochloric acid solution, saturated aqueous sodium hydrogencarbonate solution and saturated brine. The organic layer was dried over anhydrous magnesium sulfate. Removing the solvent therefrom gave 1.14 g of a viscous oil. Purifying this oil by column chromatography on silica gel (eluent, hexane:ethyl acetate=5:1) gave 0.72 g of N-[1-(4-chlorophenyl)ethyl]-2-cyano-3,3-dimethyl-5-pentenamide.

m.p. 102°–105° C.

$^1$H-NMR (CDCl$_3$/TMS): δ(ppm) 1.0–1.6 (m, 9H), 3.28 (s, 1H), 4.6–5.3 (m, 3H), 5.5–6.1 (m, 1H), 6.5–6.9 (br d, 1H), 6.95–7.4 (m, 4H).

Mass spectrum (m/e, 70 eV): 290(M$^+$), 275, 221, 178, 154, 139, 103.

PRODUCTION EXAMPLE 5

(Compound No. 18)

0.89 Gram (4 mmoles) of N-[1-(4-chlorophenyl)ethyl] -2-cyanoacetamide was dissolved in 5 ml of dry N,N-dimethylformamide (DMF) and cooled with ice. Under a nitrogen atmosphere, 0.17 g (4.2 mmoles) of sodium hydride (60% in oil) was added thereto, followed by stirring for 30 minutes with ice-cooling. Subsequently, 0.56 g (4.2 mmoles) of 3-bromo-1-butyne was added thereto and the mixture was stirred for 30 minutes with ice-cooling. Thereafter the ice bath was removed and stirring was continued for further 4 hours. After the reaction had been completed, water was added to the reaction mixture which was then extracted with ethyl acetate. The extract was washed twice with brine. The organic layer was dried and concentrated, and to the residue was added a hexane-acetonitrile solution, followed by liquid-liquid separation. Concentrating the acetonitrile layer gave 1.25 g of a resinous material. Purifying this material by column chromatography on silica gel (eluent, hexane:ethyl acetate=5:1) gave 0.50 g of N-[1-(4-chlorophenyl)ethyl]-2-cyano-3-methyl-2-pentynamide.

m.p. 75°–77° C.

$^1$H-NMR (CDCl$_3$/TMS): δ(ppm) 1.15–1.65 (m, 6H), 2.15–2.35 (m, 1H), 2.95–3.7 (m, 2H), 4.75–5.35 (m, 1H), 6.65–7 0 (br., 1H), 7.1–7.4 (m, 4H).

PRODUCTION EXAMPLE 6

(Compounds No. 37 and No. 38)

1.78 Grams (11 mmoles) of 1,1'-carbonyldiimidazole were added in small portions to a solution of 1.55 g (10 mmoles) of α-cyano-tert-butylacetic acid in 6 ml of dry tetrahydrofuran, and the mixture was stirred at room temperature for 1 hour. To this solution were added dropwise 1.56 g (10 mmoles) of R-(+)-1-(4-chlorophenyl)ethylamine, followed by stirring at room temperature for 2 hours. After the reaction had been completed, ether was added to the reaction solution which was then successively washed with a 5% aqueous hydrochloric acid solution, saturated aqueous sodium hydrogencarbonate solution and saturated brine. The organic layer was dried over anhydrous magnesium sulfate. Removing the solvent therefrom gave 2.44 g of a viscous oil. Column chromatographying this oil on silica gel (eluents, first, toluene:ethyl acetate=20:1 and then toluene:ethyl acetate=10:1) isolates 0.92 g of Compound No. 37 and 0.46 g of Compound No. 38 as crystals. Each crystal obtained was further purified by recrystallization from diisopropyl ether.

Compound No. 37 m.p. 156°–157° C.

$[α]_D^{23}$+63° (c=1, CHCl$_3$)

$^1$H-NMR (CDCl$_3$/TMS): δ(ppm) 1.10 (s, 9H), 1.44 (d, J=7 Hz, 3H), 3.09 (s, 1H), 4.65–5.25 (m, 1H), 6.47 (br d, 1H), 6.95–7.4 (m, 4H).

Mass spectrum (m/e, 70 eV): 278(M$^+$), 221, 154, 139, 103.

Elementary analysis (for C$_{15}$H$_{19}$N$_2$OCl):

|  | C | H | N | Cl |
| --- | --- | --- | --- | --- |
| Found | 64.68 | 6.85 | 10.07 | 13.2 |
| Calculated | 64.63 | 6.87 | 10.05 | 12.72 |

Compound No. 38 m.p. 140.5°–141.5° C.

$[α]_D^{23}$=+25° (c=1, CHCl$_3$) $^1$H-NMR: Same as Compound No. 37, Mass spectrum: Same as compound No. 37.

Elementary analysis (for C$_{15}$H$_{19}$N$_2$OCl):

|  | C | H | N | Cl |
| --- | --- | --- | --- | --- |
| Found | 64.69 | 6.91 | 10.07 | 12.9 |
| Calculated | 64.63 | 6.87 | 10.05 | 12.72 |

Table 1 shows some of the present compounds which can be produced by these methods.

TABLE 1

$$R-\underset{\underset{}{CH}}{\overset{CN}{|}}-\underset{\underset{}{O}}{\overset{}{C}}-\underset{}{N}-\underset{\underset{}{CH_3}}{\overset{H}{|}}-\underset{}{CH}-\underset{}{\text{(phenyl)}}-X$$

| Compound No. | R | X | Melting point (°C.), refractive index or $^1$H-NMR spectrum |
|---|---|---|---|
| (1) | $(CH_3)_3C-$ | —Cl | 99–103 |
| (2) | $(CH_3)_3C-$ | —Br | 102–104 |
| (3) | $(CH_3)_3C-$ | —CF$_3$ | 92–94 |
| (4) | CH$_3$CH$_2$CH$_2$— | —Cl | 95–97 |
| (5) | (CH$_3$)$_2$CH— | —Cl | 89–92 |
| (6) | (CH$_3$)$_2$CHCH$_2$— | —Cl | 122–125 |
| (7) | CH$_3$(CH$_3$CH$_2$)CH— | —Cl | 0.6–1.7(m, 11H), 1.8–2.4 (m, 1H), 3.15–3.55(m, 1H), 4.7–5.3(m, 1H), 6.5–6.85 (m, 1H), 7.0–7.4(m, 4H) |
| (8) | CH$_3$(CH$_3$CH$_2$CH$_2$)CH— | —Cl | 85–88 |
| (9) | cyclopentyl— | —Cl | 106–108 |
| (10) | CH$_3$CH$_2$— | —Cl | 96–98 |
| (11) | CH$_3$CH$_2$CH$_2$CH$_2$— | —Cl | 77–79 |
| (12) | (CH$_3$CH$_2$)$_2$CH— | —Cl | 73–76 |
| (13) | CH$_3$(CH$_3$CH$_2$)CH— | —Br | 0.65–1.8(m, 11H), 1.8–2.4(m, 1H), 3.0–3.5 (m, 1H), 4.7–5.3(m, 1H), 6.2–6.7(m, 1H), 6.9–7.6 (m, 4H) |
| (14) | CH$_3$(CH$_3$CH$_2$)CH— | —CF$_3$ | 0.6–1.75(m, 11H), 1.75–2.35(m, 1H), 3.1–3.55(m, 1H), 4.75–5.4 (m, 1H), 6.7–7.7(m, 5H) |

TABLE 1-continued

Structure:
R—CH(CN)—C(=O)—N(H)—CH(CH₃)—C₆H₄—X

| Compound No. | R | X | Melting point (°C.), refractive index or ¹H-NMR spectrum |
|---|---|---|---|
| (15) | cyclohexyl (CH₂—CH₂—CH₂—CH₂—CH₂—CH₂ ring, CH—) | —Cl | 149–152 |
| (16) | CH₂=CH—CH₂— | —Cl | 114–118 |
| (17) | CH≡C—CH₂— | —Cl | 96–98 |
| (18) | CH≡C—CH(CH₃)— | —Cl | 75–77 |
| (19) | CH₂=CH—CH(CH₃)— | —Cl | $n_D^{22}$ 1.5271 |
| (20) | CH₂=C(CH₃)—CH₂— | —Cl | 99–101 |
| (21) | CH₃—C(CH₃)=C—CH₂— | —Cl | 78–80 |
| (22) | CH₂=CH—C(CH₃)₂— | —Cl | 102–105 |
| (23) | CH₂=CH—C(CH₃)₂— | —Br | 100–102 |
| (24) | CH₂=CH—C(CH₃)₂— | —CF₃ | 91–94 |
| (25) | (CH₃)₃C— | —OCHF₂ | 100–105 |
| (26) | (CH₃)₃C— | —OCF₂CF₂H | 141–144 |
| (27) | (CH₃)₃C—CH₂— | —OCF₂CF₂H | 69–72 |
| (28) | (CH₃)₃C—CH₂— | —OCHF₂ | $n_D^{22}$ 1.4855 |
| (29) | (CH₃)₃C— | —OCF₃ | 91–94 |

TABLE 1-continued $$R-\underset{\underset{\text{CH}}{|}}{\overset{\overset{\text{CN}}{|}}{\text{CH}}}-\underset{\underset{\text{O}}{||}}{\text{C}}-\underset{\underset{\text{H}}{|}}{\text{N}}-\underset{\underset{\text{CH}_3}{|}}{\text{CH}}-\text{C}_6\text{H}_4-\text{X}$$

| Compound No. | R | X | Melting point (°C.), refractive index or $^1$H-NMR spectrum |
|---|---|---|---|
| (30) | (CH$_3$)$_3$C—CH$_2$— | —OCF$_3$ | 0.97(s, 9H), 1.47(d, J=7Hz, 3H), 1.70–2.0 (m, 2H), 3.1–3.4(m, 1H), 4.7–5.3(m, 1H)6.4–6.85 (br d, 1H), 6.9–7.4 (m, 4H) |
| (31) | (CH$_3$)$_2$CH— | —OCF$_2$CF$_2$H | 84–87 |
| (32) | (CH$_3$)$_2$CH— | —OCHF$_2$ | 80–83 |
| (33) | CH$_2$=CH—C(CH$_3$)$_2$— | —OCHF$_2$ | 1.2(s, 6H), 1.42(d, J=7Hz, 3H), 3.23(s, 1H), 4.65–5.25(m, 3H), 5.55–6.1(m, 1H), 6.5 (br d, 1H), 6.40(t, J=74Hz, 1H), 4.8–7.35 (m, 4H) |
| (34) | CH$_2$=CH—C(CH$_3$)$_2$— | —OCF$_3$ | 0.9–1.6(m, 9H), 3.18 (s, 1H), 4.7–5.25(m, 3H), 5.45–6.45(m, 2H), 6.85–7.35(m, 4H) |
| (35) | CH$_2$=CH—C(CH$_3$)$_2$— | —OCF$_2$CF$_2$H | 80–84 |
| (36) | (CH$_3$)$_2$CH— | —CF$_3$ | 94–97 |
| (37)*1 | (CH$_3$)$_3$C— | —Cl | 156–157, $[\alpha]_D^{23}$ (c=1, CHCl$_3$)= +63° |
| (38)*2 | (CH$_3$)$_3$C— | —Cl | 140.5–141.5, $[\alpha]_D^{23}$ (c=1, CHCl$_3$)= +25° |
| (39)*3 | (CH$_3$)$_3$C— | —Br | 115–118, $[\alpha]_D^{23}$ (c=1, CHCl$_3$)= +45° |
| (40) | (CH$_3$)$_2$CH— | —Br | 94–97 |
| (41) | (CH$_3$CH$_2$)$_2$CH— | —OCHF$_2$ | 54–58 |

TABLE 1-continued $$R-\overset{CN}{\underset{|}{CH}}-\overset{}{\underset{\parallel}{C}}-\overset{H}{\underset{|}{N}}-\overset{}{\underset{|}{CH}}-\underset{CH_3}{\bigcirc}-X$$

| Compound No. | R | X | Melting point (°C.), refractive index or $^1$H-NMR spectrum |
|---|---|---|---|
| (42) | (CH$_3$CH$_2$)$_2$CH— | —OCF$_2$CF$_2$H | 82–85 |
| (43) | (CH$_3$CH$_2$)$_2$CH— | —OCF$_3$ | 49–52 |
| (44) | (CH$_3$CH$_2$)$_2$CH— | —Br | 81–84 |
| (45) | (CH$_3$CH$_2$)$_2$CH— | —CF$_3$ | 82–85 |
| (46) | CH≡C—C(CH$_3$)$_2$— | —Cl | 147–149 |
| (47) | CH≡C—C(CH$_3$)$_2$— | —CF$_3$ | 103–107 |
| (48) | CH≡C—C(CH$_3$)$_2$— | —Br | 128–130 |
| (49) | CH≡C—C(CH$_3$)$_2$— | —OCHF$_2$ | 1.25–1.65(m, 9H), 2.37(s, 1H), 3.29 (s, 1H), 4.75–5.30 (m, 1H), 6.4–6.75 (m, 1H), 6.45(t,J= 74Hz, 1H), 6.9–7.45 (m, 4H) |
| (50) | CH≡C—C(CH$_3$)$_2$— | —OCF$_2$CF$_2$H | 68–72 |

*$^1$The absolute configuration of the amine moiety is R, and that of the acid moiety is either one of S or R. This compound is a diastereomer of Compound No. 38 and shows a larger R$_f$ value in thin layer chromatography on silica gel developed with a hexane/ethyl acetate (2:1) mixed solvent or toluene/ethyl acetate (5:1) mixed solvent.
*$^2$The absolute configuration of the amine moiety is R, and that of the acid moiety is a configuration opposite to that of Compound No. 37. This compound is a diastereomer of Compound No. 37 and shows a smaller R$_f$ value than the above in the same chromatographic system as described above.
*$^3$The absolute configuration of the amine moiety is R, and that of the acid moiety is racemic.

In Method A, the α-methylbenzylamine derivative represented by the formula (II), one of the materials for producing the present compounds, can be synthesized, for example, from a compound represented by the formula,

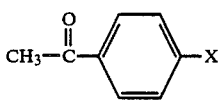

wherein X represents the same meaning as described above, according to the Leuckart's reaction described in Organic Reactions, vol. 5, 301–330 (1949).

Some of the novel α-methylbenzylamine derivatives of the formula (II) which can be obtained by this method are shown below.

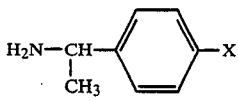

| X | ¹H-NMR (CDCl₃/TMS): δ(ppm) |
|---|---|
| —OCHF₂ | 1.32(d, J=6Hz, 3H), 1.72(s, 2H), 4.06 (q, J=6Hz, 1H), 6.43(t, J=75Hz, 1H), 6.75–7.5(m, 4H) |
| —OCF₂CF₂H | 1.32(d, J=7Hz, 3H), 2.20(s, 1H), 4.01(q, J=7Hz, 1H), 5.82(tt, J=52Hz, 3Hz, 1H), 6.9–7.45(m, 4H) |
| —OCF₃ | 1.30(d, J=7Hz, 3H), 1.48(s, 2H), 4.02(q, J=7Hz, 1H), 6.8–7.4(m, 4H) |

On the other hand, the α-substituted cyanoacetic acid represented by the formula (III) or its reactive derivative, which is the other material for producing the present compounds, can be synthesized, for example, by the method described in J. Am. Chem. Soc., 72, 4291 (1950), J. Am. Chem. Soc., 66, 886 (1944), J. Organomet. Chem., 285, 395 (1985) or J. Am. Chem. Soc., 108, 1039 (1986) and a usual method for converting to derivative, i.e. a method comprising producing a carboxylic acid by the hydrolysis of a carboxylic acid ester [e.g., Arkiv Kemi, 2, 321 (1950)] followed by producing a carboxylic acid halide by the acid-halogenation of a carboxylic acid [e.g., Tetrahedron, 35, 1965 (1979)].

In Method B, the cyanoacetamide derivative represented by the formula (IV), one of the materials for producing the present compounds, can be obtained by reacting the α-methylbenzylamine derivative represented by the formula (II) with a cyanoacetic acid or its reactive derivative in the presence of a reaction assistant if necessary.

Some of the cyanoacetamide derivatives of the formula (IV) which can be obtained by this method are shown below.

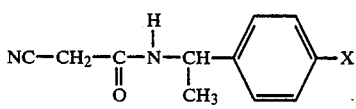

| X | m.p. (°C.) |
|---|---|
| Cl | 133 |
| Br | 136–139 |
| CF₃ | 131–133 |

For the alkylating agent represented by the formula (V), which is the other material for producing the present compounds, the commercially available product may be used, or it can be synthesized from the commercially available material according to a usual method.

The present compounds have at least two asymmetric carbon atoms and at least four stereoisomers. They also include the optical isomers in which the absolute configuration of the benzyl position is R. In this case, optically active α-methylbenzylamine derivatives, one of the materials, represented by the formula (II) and having an absolute configuration of R in the benzyl position can be obtained, for example, by the optical resolution of the corresponding racemates according to the method described in J. Chem. Soc. (B), 1971, 2418.

When the present compounds may be used as an active ingredient for plant disease protectants, they may be used as they are without adding any other ingredients. Usually, however, they are formulated before use into emulsifiable concentrates, wettable powders, suspension formulations, granules, dusts, etc. by mixing with solid carriers, liquid carriers, surface active agents and other auxiliaries for formulation.

These preparations contain from 0.1 to 99% by weight, preferably from 0.2 to 95% by weight of the present compounds as an active ingredient.

The solid carriers include fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide, etc. The liquid carriers include aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton seed oil), dimethyl sulfoxide, acetonitrile, water, etc.

The surface active agents used for emulsification, dispersion, wetting, etc. include anionic surface active agents such as the salt of alkyl sulfates, alkyl(aryl)sulfonates, dialkyl sulfosuccinates, the salt of polyoxyethylene alkylaryl ether phosphoric acid esters, naphthalenesulfonic acid/formalin condensates, etc. and nonionic surface active agents such as polyoxyethylene alkyl ether, polyoxyethylene polyoxypropylene block copolymers, sorbitan fatty acid esters, polyoxyethylene sorbitan fatty acid esters, etc.

The auxiliaries for formulation include lignosulfonates, alginates, polyvinyl alcohol, gum arabic, CMC (carboxymethyl cellulose), PAP (isopropyl acid phosphate), etc.

These preparations are used as they are, or used for foliage application in dilution with water, soil incorporation by dusting or granule application, soil application, etc. An increase in the controlling activity can be expected by using them in mixture with other plant disease controlling agents. These preparations can be used in mixture with insecticides, acaricides, nematocides, herbicides, plant growth regulators, fertilizers, soil improvers, etc.

When the present compounds are used as an active ingredient for plant disease controlling agents, their dosage rate varies with weather conditions, preparation forms, when, how and where they are applied, diseases to be controlled, crops to be protected, etc. However it is usually from 0.05 to 200 g/are, preferably from 0.1 to 100 g/are. When the emulsifiable concentrates, wettable powders, suspension formulations, etc. are applied in dilution with water, the application concentration of the present compounds is from 0.00005 to 0.5%, preferably from 0.0001 to 0.2%. The granules, dusts, etc. are applied as they are without dilution.

The present invention is illustrated in more detail with reference to the following formulation examples and test examples, but it is not limited to these examples.

Formulation examples are shown below. In the examples, the present compounds are identified by Compound No. in Table 1, and parts are by weight.

FORMULATION EXAMPLE 1

Mixing and well pulverizing 50 parts of each of the present compounds (1) to (50), 3 parts of calcium lignosulfonate, 2 parts of sodium lauryl sulfate and 45 parts of synthetic hydrated silicon dioxide gives a wettable powder of each compound.

FORMULATION EXAMPLE 2

Mixing and wet-pulverizing 25 parts of each of the present compounds (1) to (50), 3 parts of polyoxyethylene sorbitan monooleate, 3 parts of CMC and 69 parts of water until the particle size of the active ingredient is reduced to 5 microns or less gives a suspension formulation of each compound.

FORMULATION EXAMPLE 3

Mixing and well pulverizing 2 parts of each of the present compounds (1) to (50), 88 parts of kaolin clay and 10 parts of talc gives a dust of each compound.

FORMULATION EXAMPLE 4

Well mixing 20 parts of each of the present compounds (1) to (50), 14 parts of polyoxyethylene styrylphenyl ether, 6 parts of calcium dodecylbenzene-sulfonate and 60 parts of xylene gives an emulsifiable concentrate of each compound.

FORMULATION EXAMPLE 5

Mixing and well pulverizing 2 parts of each of the present compounds (1) to (50), 1 part of synthetic hydrated silicon dioxide, 2 parts of calcium lignosulfonate, 30 parts of bentonite and 65 parts of kaolin clay followed by well kneading with water, granulating and drying gives a granule of each compound.

The following test examples demonstrate the usefulness of the present compounds as a plant disease protectant. In the test examples, the present compounds are identified by Compound No. in Table 1, and compounds used as a control as identified by Compound symbol in Table 2.

TABLE 2

| Compound symbol | Structural formula | Remarks |
|---|---|---|
| A | $CH_3-C(CH_3)(CH_3)-C(CN)=C(O)-N(H)-C(CH_3)(CH_3)-C_6H_5$ | Compound disclosed in JP-A-63-72663. |
| B | $(iso-C_3H_7O)_2P(O)-SCH_2-C_6H_5$ | Commercial product (IBP) |

The following six stages, 5, 4, 3, 2, 1, 0, express the controlling activity according to the condition of disease of test plants at the time of examination, i.e. the macroscopically observed degrees of colony and infected area on the leaves, stems, etc.

5 No colony nor infected area is observed.
4 About 10% of colony or infected area is observed.
3 About 30% of colony or infected area is observed.
2 About 50% of colony or infected area is observed.
1 About 70% of colony or infected area is observed.
0 More than about 70% of colony or infected area is observed, there being no difference in the condition of disease between the treated and untreated plots.

TEXT EXAMPLE 1

Controlling Test on Rice Blast (*Pyricularia oryzae*) (preventive effect)

Sandy loam was filled in plastic pots, and rice (var., Kinki No. 33) was sowed and cultivated into seedlings for 20 days in a greenhouse. The wettable powder of each test compound prepared according to Formulation example 1 was diluted with water to a prescribed concentration and foliar-applied onto the seedlings so that the spray liquor was thoroughly attached to the leaf surface. After the spraying, the seedlings were air-dried and inoculated by spraying the spore suspension of *Pyricularia oryzae*. After the inoculation, the seedlings were cultivated at 28° C. under a dark and highly humid condition for 4 days to examine the controlling activity. Table 3 shows the results.

TABLE 3

| Test compound | | |
|---|---|---|
| Compound No. | Application concentration of active ingredient (ppm) | Controlling activity |
| (1) | 500 | 5 |
| (2) | 500 | 5 |
| (3) | 500 | 5 |
| (4) | 500 | 5 |
| (5) | 500 | 5 |
| (6) | 500 | 5 |
| (7) | 500 | 5 |
| (8) | 500 | 5 |
| (9) | 500 | 5 |
| (10) | 500 | 5 |
| (11) | 500 | 5 |
| (12) | 500 | 5 |
| (13) | 500 | 5 |
| (14) | 500 | 5 |
| (15) | 500 | 5 |
| (18) | 500 | 5 |
| (19) | 500 | 5 |
| (20) | 500 | 5 |
| (21) | 500 | 5 |
| (22) | 500 | 5 |
| (23) | 500 | 5 |
| (24) | 500 | 5 |
| (25) | 500 | 5 |
| (26) | 500 | 5 |
| (27) | 500 | 5 |
| (28) | 500 | 5 |
| (29) | 500 | 5 |
| (30) | 500 | 5 |
| (31) | 500 | 5 |
| (32) | 500 | 5 |
| (33) | 500 | 5 |
| (34) | 500 | 5 |
| (35) | 500 | 5 |
| (36) | 500 | 5 |
| (37) | 500 | 5 |
| (38) | 500 | 5 |
| (39) | 500 | 5 |
| (40) | 500 | 5 |
| (41) | 500 | 5 |
| (42) | 500 | 5 |
| (43) | 500 | 5 |
| (44) | 500 | 5 |
| (45) | 500 | 5 |
| (46) | 500 | 5 |
| (47) | 500 | 5 |
| (48) | 500 | 5 |
| (49) | 500 | 5 |
| (50) | 500 | 5 |
| (A) | 500 | 0 |
| (B) | 500 | 4 |

TEST EXAMPLE 2

Controlling Test on Rice Blast (*Pyricularia oryzae*) (systemic effect)

Sandy loam was filled in plastic pots, and rice (var., Kinki No. 33) was sowed and cultivated into seedlings for 14 days in a greenhouse. The emulsifiable concentrate of each test compound prepared according to Formulation example 4 was diluted with water, and the soil was drenched with a prescribed amount of this aqueous dilute solution. After the drenching, the seedlings were cultivated for 7 days in a greenhouse and inoculated by spraying the spore suspension of *Pyricularia oryzae*. After the inoculation, the seedlings were allowed to stand at 28° C. under a dark and highly humid condition for 4 days to examine the controlling activity. Table 4 shows the results.

TABLE 4

| Test compound | | |
|---|---|---|
| Compound No. | Application concentration of active ingredient (g/10 ares) | Controlling activity |
| (1) | 500 | 5 |
| (2) | 500 | 5 |
| (3) | 500 | 5 |
| (4) | 500 | 5 |
| (5) | 500 | 5 |
| (6) | 500 | 5 |
| (7) | 500 | 5 |
| (8) | 500 | 5 |
| (9) | 500 | 5 |
| (10) | 500 | 5 |
| (11) | 500 | 5 |
| (12) | 500 | 5 |
| (13) | 500 | 5 |
| (14) | 500 | 5 |
| (16) | 500 | 5 |
| (17) | 500 | 5 |
| (18) | 500 | 5 |
| (19) | 500 | 5 |
| (20) | 500 | 5 |
| (22) | 500 | 5 |
| (23) | 500 | 5 |
| (24) | 500 | 5 |
| (25) | 500 | 5 |
| (26) | 500 | 5 |
| (27) | 500 | 5 |
| (28) | 500 | 5 |
| (29) | 500 | 5 |
| (30) | 500 | 5 |
| (31) | 500 | 5 |
| (32) | 500 | 5 |
| (33) | 500 | 5 |
| (34) | 500 | 5 |
| (35) | 500 | 5 |
| (36) | 500 | 5 |
| (37) | 500 | 5 |
| (38) | 500 | 5 |
| (39) | 500 | 5 |
| (40) | 500 | 5 |
| (41) | 500 | 5 |
| (43) | 500 | 5 |
| (44) | 500 | 5 |
| (45) | 500 | 5 |
| (46) | 500 | 5 |
| (47) | 500 | 5 |
| (48) | 500 | 5 |
| (49) | 500 | 5 |
| (50) | 500 | 5 |
| (A) | 500 | 0 |
| (B) | 500 | 4 |

TEST EXAMPLE 3

Controlling Test on Scab of Apple (*Venturia inaequalis*) (preventive effect)

Sandy loam was filled in plastic pots, and apple was sowed and cultivated into seedlings for 20 days in a greenhouse. The emulsifiable concentrate of each test compound prepared according to Formulation example 4 was diluted with water to a prescribed concentration and foliar-applied onto the seedlings so that the spray liquor was thoroughly attached to the leaf surface. After the spraying, the seedlings were inoculated by spraying the spore suspension of *Venturia inaequalis*. After the inoculation, the seedlings were firstly allowed to stand at 15° C. under a highly humid condition for 4 days and then cultivated under lighting for 15 days to examine the controlling activity. Table 5 shows the results.

TABLE 5

| Test compound | | |
|---|---|---|
| Compound No. | Application concentration of active ingredient (ppm) | Controlling activity |
| (1) | 500 | 4 |
| (2) | 500 | 5 |
| (3) | 500 | 4 |
| (12) | 500 | 5 |
| (13) | 500 | 4 |
| (37) | 500 | 4 |
| (38) | 500 | 5 |
| (39) | 500 | 4 |
| (A) | 500 | 0 |

TEST EXAMPLE 4

Controlling Test on Anthracnose of Cucumber (*Colletotrichum lagenarium*) (preventive effect)

Sandy loam was filled in plastic pots, and cucumber (var., Sagami-hanjiro) was sowed and cultivated into seedlings iu the cotyledonous stage for 14 days in a greenhouse. The wettable powder of each test compound prepared according to Formulation Example 1 was diluted with water to a prescribed concentration and foliar-applied onto the seedlings so that the spray liquor was thoroughly attached to the leaf surface. After the spraying, the seedlings were air-dried and inoculated by spraying the spore suspension of *Colletotrichum lagenarium*. After the inoculation, the seedlings were firstly allowed to stand at 23° C. under a highly humid condition for 1 day and then cultivated under lighting for 4 days to examine the controlling activity. Table 6 shows the results.

TABLE 6

| Test compound | | |
|---|---|---|
| Compound No. | Application concentration of active ingredient (ppm) | Controlling activity |
| (1) | 500 | 4 |
| (2) | 500 | 5 |
| (3) | 500 | 4 |
| (37) | 500 | 4 |
| (38) | 500 | 5 |
| (39) | 500 | 4 |
| (A) | 500 | 0 |

What is claimed is:

1. A cyanoacetamide derivative represented by the formula

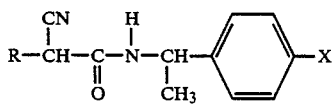

wherein R represents a tertiary butyl, $C_2$–$C_5$ primary alkyl, $C_2$–$C_5$ secondary alkyl or cycloalkyl and X represents halogen, cyano, or trifluoromethyl.

2. A cyanoacetamide derivative represented by the formula,

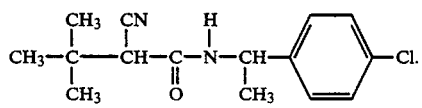

3. A cyanoacetamide derivative represented by the formula

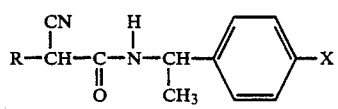

wherein R represents $C_2$–$C_6$ alkenyl or $C_2$–$C_6$ alkynyl and X represents chlorine, bromine, trifluoromethyl or lower fluoroalkoxy.

4. A cyanoacetamide derivative represented by the formula,

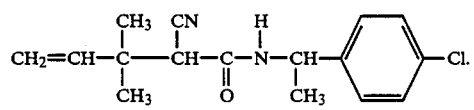

5. A cyanoacetamide derivative represented by the formula,

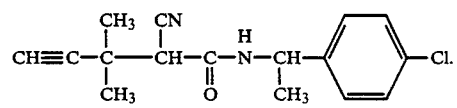

6. A plant disease protectant which comprises as an active ingredient an effective amount of a cyanoacetamide derivative of claim 1 together with an inert carrier or diluent.

7. A method for controlling plant pathogenic fungi which comprises applying an effective amount of a cyanoacetamide derivative of claim 1 to plant pathogenic fungi.

8. A method according to claim 7, wherein the plant pathogenic fungi are *Pyricularia oryzae*.

9. A plant disease protectant which comprises as an active ingredient an effective amount of a cyanoacetamide derivative of claim 2 together with an inert carrier or diluent.

10. A plant disease protectant which comprises as an active ingredient an effective amount of a cyanoacetamide derivative of claim 4 together with an inert carrier or diluent.

11. A plant disease protectant which comprises as an active ingredient an effective amount of a cyanoacetamide derivative of claim 5 together with an inert carrier or diluent.

12. A method for controlling plant pathogenic fungi which comprises applying an effective amount of a cyanoacetamide derivative of claim 2 to plant pathogenic fungi.

13. A method for controlling plant pathogenic fungi which comprises applying an effective amount of a cyanoacetamide derivative of claim 4 to plant pathogenic fungi.

14. A method for controlling plant pathogenic fungi which comprises applying an effective amount of a cyanoacetamide derivative of claim 5 to plant pathogenic fungi.

15. A plant disease protectant which comprises as an active ingredient an effective amount of a cyanoacetamide derivative of claim 3 together with an inert carrier or diluent.

16. A method for controlling plant pathogenic fungi which comprises applying an effective amount of a cyanoacetamide derivative of claim 3 to plant pathogenic fungi.

17. A method according to claim 16, wherein the plant pathogenic fungi are *Pyricularia oryzae*.

18. A cyanoacetamide derivative having the formula:

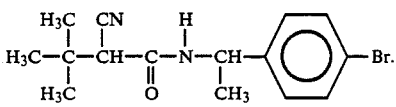

19. A cyanoacetamide derivative having the formula,

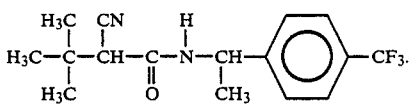

20. A cyanoacetamide derivative having the formula,

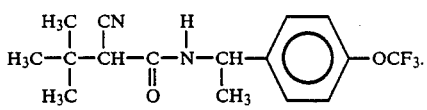

* * * * *